US012630583B2

(12) United States Patent
Chen et al.

(10) Patent No.: US 12,630,583 B2
(45) Date of Patent: May 19, 2026

(54) METHODS OF PURIFYING PROTEINS USING CHROMATOGRAPHY

(71) Applicant: Bristol-Myers Squibb Company, Princeton, NJ (US)

(72) Inventors: Zhiqiang Chen, Boxborough, MA (US); Xuankuo Xu, Boxborough, MA (US); Sanchayita Ghose, Acton, MA (US); Zhengjian Li, Sudbury, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1274 days.

(21) Appl. No.: 17/250,229

(22) PCT Filed: Jun. 18, 2019

(86) PCT No.: PCT/US2019/037806
§ 371 (c)(1),
(2) Date: Dec. 18, 2020

(87) PCT Pub. No.: WO2019/246153
PCT Pub. Date: Dec. 26, 2019

(65) Prior Publication Data
US 2021/0122783 A1     Apr. 29, 2021

Related U.S. Application Data

(60) Provisional application No. 62/687,164, filed on Jun. 19, 2018.

(51) Int. Cl.
C07K 1/36          (2006.01)
C07K 16/00        (2006.01)
(52) U.S. Cl.
CPC ................ C07K 1/36 (2013.01); C07K 16/00 (2013.01)

(58) Field of Classification Search
CPC ........ C07K 1/36; C07K 16/00; C07K 16/065; C07K 1/18; C07K 1/165; C07K 1/22; C07K 14/00
See application file for complete search history.

(56) References Cited

U.S. PATENT DOCUMENTS

2013/0289247 A1* 10/2013 Kremer .................. C07K 16/00
                                                                  530/387.1
2014/0018525 A1      1/2014 Goklen et al.
(Continued)

FOREIGN PATENT DOCUMENTS

CN          103547589 A      1/2014
CN          105669829 A      6/2016
(Continued)

OTHER PUBLICATIONS

Ichihara et al. Integrated flow-through purification for therapeutic monoclonal antibodies processing. MAbs 2018, vol. 10, Issue 2, pp. 325-334. (Year: 2018).*
(Continued)

*Primary Examiner* — Shafiqul Haq
(74) *Attorney, Agent, or Firm* — Sterne, Kessler, Goldstein & Fox P.L.L.C.

(57)          ABSTRACT

This disclosure provides a method of purifying proteins using a combined AEX-CEX chromatography in flow-through mode under an operating condition wherein no automation, engineering control, and/or in-line adjustment is used between the AEX and the CEX. The AEX and CEX (or CEX and AEX) can be connected directly.

12 Claims, 4 Drawing Sheets

CEX or AEX

AEX or CEX

(56) References Cited

U.S. PATENT DOCUMENTS

| | | |
|---|---|---|
| 2016/0016992 A1 | 1/2016 | Bian et al. |
| 2017/0198008 A1 | 7/2017 | Blank et al. |
| 2018/0078876 A1 | 3/2018 | Wang et al. |

FOREIGN PATENT DOCUMENTS

| | | |
|---|---|---|
| CN | 106794392 A | 5/2017 |
| CN | 107636005 A | 1/2018 |
| JP | 2010535499 A | 11/2010 |
| JP | 2013503877 A | 2/2013 |
| JP | 2014520814 A | 8/2014 |
| JP | 2017132757 A | 8/2017 |
| WO | WO-2009020389 A1 | 9/2009 |
| WO | WO-2010019148 A1 | 2/2010 |
| WO | WO-2011028753 A1 | 3/2011 |
| WO | WO-2012059308 A1 | 5/2012 |
| WO | WO-2013068603 A2 | 5/2013 |
| WO | WO-2018047906 A1 | 3/2018 |

OTHER PUBLICATIONS

Yamada et al. Purification of monoclonal antibodies entirely in flow-through mode. Journal of Chromatography B 1061-1062 (2017) 110-116 (Year: 2017).*

Teshima, G., et al., "Separation of oxidized variants of a monoclonal antibody by anion-exchange," J Chromatogr A 1218(15):2091-2097, Elsevier, Netherlands (Apr. 2011).

Bird, R.E., et al., "Single-chain antigen-binding proteins," *Science* 242(4877):423-426, Association for the Advancement of Science, United States (Oct. 1988).

Boyle, M. D. P., et al., "Applications of Bacterial Immunoglobulin-Binding Proteins to the Purification of Immunoglobulins" in *Molecular Interactions in Bioseparations*, pp. 91-112, Ngo, T. T., ed., Plenum Press, United States (1993).

Hou, K. C., et al., "Protein A immobilized affinity cartridge for immunoglobulin purification," *Biotechnology and Applied Biochemistry* 13(2):257-268, Wiley-Blackwell, United States (Apr. 1991).

Huston, J.S., et al., "Protein engineering of antibody binding sites: recovery of specific activity in an anti-digoxin single-chain Fv analogue produced in *Escherichia coli*," *Proceedings of the National Academy of Sciences USA* 85(16):5879-5883, National Academy of Sciences, United States (Aug. 1988).

Shukla, A.A., et al., "Downstream Processing of Monoclonal Antibodies—Application of Platform Approaches," *Journal of Chromatography B* 848(1):28-39, Elsevier, Netherlands (Mar. 2007).

Ward, E.S., et al., "Binding Activities of a Repertoire of Single Immunoglobulin Variable Domains Secreted from *Escherichia coli*," *Nature* 341(6242):544-546, Nature Publishing Group, United Kingdom (Oct. 1989).

International Search Report and Written Opinion for Application No. PCT/US2019/037806, European Patent Office, Netherlands, mailed on Nov. 14, 2019, 19 pages.

Laursen, I.A., et al., "Development, manufacturing and characterization of a highly purified, liquid immunoglobulin g preparation from human plasma," Transfusion Medicine and Hemotherapy 41(3):205-212, S. Karger, Switzerland (Jun. 2014).

\* cited by examiner

CEX or AEX

AEX or CEX

METHODS OF PURIFYING PROTEINS USING CHROMATOGRAPHY

BACKGROUND OF THE DISCLOSURE

Large-scale, efficient, and economic purification of proteins represents one of the major hurdles to overcome in the current biotechnology and pharmaceutical industries. Generally, the production and purification occurs first with various "upstream" cell culture processes to produce a protein of interest. After production, "downstream" purification processes are employed to separate and isolate the protein of interest from any undesirable contaminants that may also be present in the mixture produced in the upstream process. Various upstream and downstream techniques can be found, for example, in *Biopharmaceutical Processing: Development, Design, and Implementation of Manufacturing* Processes, Jagschies et al., 2017. A specific subset of proteins, monoclonal antibodies (mAbs) and their derivative products (e.g., Fc-fusion proteins, bispecific antibodies), play an important role in treating some of the most challenging human diseases owing to the safety, efficacy and high quality of these types of biologics. The manufacturing of mAbs begins with the protein expression in recombinant mammalian cultures. The cell culture broth is then harvested through direct depth filtration or centrifugation. The clarified bulk is then subjected to downstream purification (DSP). Downstream purification processes typically use Protein A chromatography for capture, followed by one or two polishing steps as described in Shukla et al., *Downstream Processing Of Monoclonal Antibodies—Application Of Platform Approaches,* J Chromatogr B Analyt Technol Biomed Life Sci, 848 (2007) 28-39. Cation-exchange (CEX), anion-exchange (AEX), hydrophobic interaction (HIC) and mixed mode chromatography have all been used as polishing steps.

Current downstream purifications are often performed as batch processes with hold tanks between different unit operations (chromatography and filters). Necessary buffer adjustment (e.g., pH or conductivity adjustment) is often needed for each unit operation. Automation and in-line adjustment of eluates have been reported to improve the purification steps. Nonetheless, the in-line adjustments of the buffer condition can be cumbersome and increase the operation cost and time and skid footprint.

SUMMARY OF THE DISCLOSURE

The present disclosure is related to a combined chromatography process for the continuous purification of a protein of interest wherein an AEX and CEX are operated in flow-through mode, without any in-line adjustments to chromatography conditions including pH and/or conductivity. One aspect of the present disclosure is directed to purification of a protein of interest using an AEX-CEX or CEX-AEX purification approach wherein there is no in-line adjustment to any of the purification conditions, including pH or conductivity. Specifically, the approach uses cation exchange chromatography (CEX) and anion exchange chromatography (CEX) in tandem, either in AEX-CEX or CEX-AEX order. In some embodiments, the AEX and CEX have no adjustments made to the pH or the conductivity of the in-process pool between the AEX and CEX, or CEX and AEX. Another feature of the disclosure is that the column conditions of the AEX and CEX are processed together and operated as a single unit, which greatly reduces process cost, process operation time, and the process skid footprint.

In some embodiments, the protein has an isoelectric point (pI) higher than about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In other embodiments, the protein has an isoelectric point (pI) lower than about 12.0, about 11.9, about 11.8, about 11.7, about 11.6, about 11.5, about 11.4, about 11.3, about 11.2, about 11.1, about 11.0, about 10.9, about 10.8, about 10.8, about 10.7, about 10.6, about 10.5, about 10.4, about 10.3, about 10.2, about 10.1, or about 10.0.

In some embodiments, the protein has a pI between about 7.0 and about 11.0, between about 7.0 and about 10.0, between about 6.5 and about 10.5, or between about 7.2 and about 9.6. In other embodiments, the protein has a pI of about 6.5, about 7.0, about 7.5, about 8.0, about 8.0, about 8.5, about 9.0, about 9.5, about 10.0, about 10.5, or about 11.0. In other embodiments, the protein has an isoelectric point (pI) lower than about 6.5, about 6.4, about 6.3, about 6.2, about 6.1, about 5.9, about 5.8, or about 5.7.

In some embodiments, the protein has an isoelectric point (pI) higher than about 1.0, about 2.0, about 3.0, about 4.0, or about 5.0. In other embodiments, the protein has a pI between about 1.0 and about 6.5, between about 2.0 and about 6.0, between about 2.5 and about 6.5, or between about 2.0 and about 5.8. In other embodiments, the protein has a pI of about 6.5, about 6.4, about 6.3, about 6.2, about 6.1, about 6.0, about 5.9, about 5.8, about 5.7, about 5.6, or about 5.5.

In some embodiments, the combined chromatography comprises adding a loading buffer and adding a chase buffer.

In some embodiments, the loading buffer has a pH higher than about 6.0, about 6.5, about 7.0, about 7.5, about 8.0, about 8.5, about 9.0, about 9.5, or about 10.0. In other embodiments, the loading buffer has a pH between about 6.0 and about 11.0, between about 6.5 and about 11.0, between about 7.0 and about 10.5, between about 7.0 and about 10.0, between about 7.0 and about 9.5, between about 7.0 and about 9.0, between about 7.0 and about 8.5, between about 7.0 and about 8.0, or between about 7.0 and about 7.5. In other embodiments, the loading buffer has a pH of about 6.5, about 7.0, about 7.2, about 7.4, about 7.6, about 7.8, about 8.0, about 8.2, about 8.4, about 8.6, about 8.8, about 9.0, about 9.2, about 9.4, about 9.6, about 9.8, about 10.0, about 10.5, about 11.0, or about 11.5.

In some embodiments, the chase buffer has a pH higher than about 6.0, about 6.5, higher than about 7.0, about 7.5, about 8.0, about 8.5, or about 9.0. In other embodiments, the chase buffer has a pH between about 6.0 and about 11.0. between about 6.5 and about 10.0, between about 7.0 and about 11.0, between about 7.0 and about 10.0, between about 7.0 and about 9.0, between about 7.0 and about 8.0, between about 7.0 and about 8.5, between about 7.0 and about 9.5, between about 6.5 and about 8.5, or between about 6.5 and about 7.5. In other embodiments, the chase buffer has a pH of about 6.0, about 6.2, about 6.4, about 6.6, about 6.8, about 7.0, about 7.2, about 7.4, about 7.6, about 7.8, about 8.0, about 8.2, about 8.4, about 8.6, about 8.8 or about 9.0.

In some embodiments, the chase buffer has a pH that is the same as or different from the pH of the loading buffer.

In some embodiments, the loading buffer has a conductivity between about 0.1 mS/cm to about 9.0 mS/cm, between about 0.5 mS/cm to about 9.0 .mS/cm, between about 1.0 to about 9.0 mS/cm, between about 2.0 to about 8.0 mS/cm, between about 2.0 to about 7.0 mS/cm, between about 2.0 to about 8.5 mS/cm, between about 2.0 to about 7.5 mS/cm, or between about 2.5 to about 7.0 mS/cm. In other embodiments, the loading buffer has a conductivity of about 0.1 mS/cm, about 0.5 mS/cm, about 1.0 mS/cm, about 1.5 mS/cm, about 2.0 mS/cm, about 2.5 mS/cm, about 3.0 mS/cm, about 3.5 mS/cm, about 4.0 mS/cm, about 4.5 mS/cm, about 5.0 mS/cm, about 5.5 mS/cm, about 6.0 mS/cm, about 6.5 mS/cm, about 7.0 mS/cm, about 7.5 mS/cm, about 8.0 mS/cm, about 8.5 mS/cm, or about 9.0 mS/cm.

In some embodiments, the loading buffer has a conductivity between about 6.0 mS/cm to about 15.0 mS/cm, between about 6.5 mS/cm to about 15 mS/cm, between about 7.0 mS/cm to about 14.0 mS/cm, between about 8.0 mS/cm to about 13.0 mS/cm, between about 9.0 mS/cm to about 12.0 mS/cm, or between about 9.0 mS/cm and about 9.5 mS/cm. In other embodiments, the loading buffer has a conductivity of about 6.0 mS/cm, about 6.5 mS/cm, about 7.0 mS/cm, about 7.5 mS/cm, about 8.0 mS/cm, about 8.5 mS/cm, about 9.0 mS/cm, about 9.5 mS/cm, about 10.0 mS/cm, about 10.5 mS/cm, about 11.0 mS/cm, about 11.5 mS/cm, about 12.0 mS/cm, about 12.5 mS/cm, about 13.0 mS/cm, about 13.5 mS/cm, about 14.0 mS/cm, about 14.5 mS/cm, or about 15.0 mS/cm.

In some embodiments, the chase buffer has a conductivity between about 0.1 mS/cm to about 9.0 mS/cm, between about 0.5 mS/cm to about 9.0 mS/cm, between about 1.0 to about 9.0 mS/cm, between about 2.0 to about 8.0 mS/cm, between about 2.0 to about 7.0 mS/cm, between about 2.0 to about 8.5 mS/cm, between about 2.0 to about 7.5 mS/cm, or between about 2.5 to about 7.0 mS/cm. In other embodiments, the chase buffer has a conductivity of about 0.1 mS/cm, of about 0.5 mS/cm, about 1.0 mS/cm, about 1.5 mS/cm, about 2.0 mS/cm, about 2.5 mS/cm, about 3.0 mS/cm, about 3.5 mS/cm, about 4.0 mS/cm, about 4.5 mS/cm, about 5.0 mS/cm, about 5.5 mS/cm, about 6.0 mS/cm, about 6.5 mS/cm, about 7.0 mS/cm, about 7.5 mS/cm, about 8.0 mS/cm, about 8.5 mS/cm, or about 9.0 mS/cm. In other embodiments, the chase buffer has a conductivity between about 6.0 mS/cm to about 15.0 mS/cm, between about 6.5 mS/cm to about 15.0 mS/cm, between about 7.0 to about 15.0 mS/cm, between about 8.0 to about 14.0 mS/cm, between about 8.0 to about 13.0 mS/cm, between about 8.0 to about 14.5 mS/cm, between about 8.0 to about 13.5 mS/cm, or between about 8.5 to about 13.0 mS/cm. In other embodiments, the chase buffer has a conductivity of about 6.0 mS/cm, of about 6.5 mS/cm, about 7.0 mS/cm, about 7.5 mS/cm, about 8.0 mS/cm, about 8.5 mS/cm, about 9.0 mS/cm, about 9.5 mS/cm, about 10.0 mS/cm, about 10.5 mS/cm, about 11.0 mS/cm, about 11.5 mS/cm, about 12.0 mS/cm, about 12.5 mS/cm, about 13.0 mS/cm, about 13.5 mS/cm, about 14.0 mS/cm, about 14.5 mS/cm, or about 15.0 mS/cm.

In some embodiments, the conductivity of the chase buffer is higher than, lower than, or same as the conductivity of the loading buffer. In some embodiments, the conductivity of the chase buffer is at least 0.1 mS/cm, at least 0.2 mS/cm, at least 0.3 mS/cm, at least 0.4 mS/cm, at least 0.5 mS/cm, at least 1.0 mS/cm, at least 1.5 mS/cm, at least 2.0 mS/cm, at least 2.5 mS/cm, at least 3.0 mS/cm, at least 3.5 mS/cm, at least 4.0 mS/cm, at least 4.5 mS/cm, or at least 5.0 mS/cm, higher than the conductivity of the loading buffer.

In some embodiments, the mixture comprises one or more contaminants. In some embodiments, the contaminants comprise host cell proteins (HCP), DNA, high molecular weight species (HMW), low molecular weight species (LMW), residual protein A (rPA), or any combination thereof.

In some embodiments, the chromatography reduces the level of contaminants. In some embodiments, the combined chromatography reduces the HCP level to about 100 ppm or lower, about 90 ppm or lower, about 80 ppm or lower, about 70 ppm or lower, about 60 ppm or lower, about 50ppm or lower, about 40 ppm or lower, about 30 ppm or lower, about 20 ppm or lower, or about 10 ppm or lower. In some embodiments, the combined chromatography reduces the HMW level to about 1.0% or lower, about 0.9% or lower, about 0.8% or lower, about 0.7% or lower, about 0.6% or lower, about 0.5% or lower, about 0.4% or lower, about 0.3% or lower, about 0.2% or lower or about 0.1% or lower. In some embodiments, the combined chromatography reduces the LMW level to about 1.0% or lower, about 0.9% or lower, about 0.8% or lower, about 0.7% or lower, about 0.6% or lower, about 0.5% or lower, about 0.4% or lower, about 0.3% or lower, about 0.2% or lower or about 0.1% or lower. In some embodiments, the combined chromatography reduces the DNA level to about 20 pg/mL or lower, about 18 pg/mL or lower, about 16 pg/mL or lower, about 14 pg/mL or lower, about 12 pg/mL or lower, about 10 pg/mL or lower, about 8 pg/mL or lower, about 6 pg/mL or lower, about 4 pg/mL or lower, or about 2 pg/mL or lower. In some embodiments, the combined chromatography reduces the residual Protein A (rPA) level to about 6 ppm or lower, about 5 ppm or lower, about 4 ppm or lower, about 3 ppm or lower, about 2 ppm or lower, about 1 ppm or lower, about 0.8 ppm or lower, about 0.6 ppm or lower, about 0.5 ppm or lower, about 0.4 ppm or lower, about 0.3 ppm or lower, about 0.2 ppm or lower or about 0.1 ppm or lower.

Also described herein is a method of reducing or removing a post-loading step buffer transition peak in a chromatography, the method comprising adding a loading buffer and a chase buffer during the chromatography for purifying a protein in a mixture, wherein the chase buffer has higher conductivity than the loading buffer. In some embodiments, the chromatography is an AEX chromatography, a CEX chromatography, a combined AEX and CEX chromatography, or a combined CEX and AEX chromatography. In some embodiments, the chromatography is in flow-through mode. In some embodiments, the loading buffer has a conductivity between about 3.0 mS/cm and about 6.0 mS/cm, and the chase buffer has a conductivity between about 6.0 mS/cm and about 12.0 mS/cm. In some embodiments, wherein the conductivity of the chase buffer is at least 0.5 mS/cm, at least 1.0 mS/cm, at least 1.5 mS/cm, at least 2.0 mS/cm, at least 2.5 mS/cm, at least 3.0 mS/cm, at least 3.5 mS/cm, at least 4.0 mS/cm, at least 4.5 mS/cm, or at least 5.0 mS/cm, higher than the conductivity of the loading buffer. In a specific embodiment, the loading buffer has a conductivity of 5.0 mS/cm and the chase buffer has a conductivity of 6.0 mS/cm. In some embodiments, the loading buffer comprises sodium chloride, ammonium chloride, potassium chloride, sodium acetate, ammonium acetate, sodium sulfate, ammonium sulfate, ammonium thiocyanate, sodium citrate, sodium phosphate, and potassium, magnesium, and calcium salts thereof, or any combinations thereof. In a specific embodiment, the loading buffer comprises sodium acetate-Tris. In other embodiments, the chase buffer comprises sodium chloride, ammonium chloride, potassium chloride, sodium acetate, ammonium acetate, sodium sulfate, ammonium sulfate, ammonium thiocyanate, sodium citrate, sodium phosphate, and potassium, magnesium, and calcium salts thereof, or any combinations thereof. In a specific embodiment, the chase buffer comprises sodium acetate-Tris. In some embodiments, the chromatography comprises columns that are loaded to 50 g/L resin, 100 g/L resin, 150 g/L resin, 200 g/L resin, 250 g/L resin, 300g/L resin, 350 g/L resin, 400 g/L resin, 450 g/L resin, or 500 g/L resin.

In some embodiments, the chromatography comprises a CEX resin selected from Poros HS, Poros XS, carboxymethyl-cellulose, BAKERBOND ABX™, sulphopropyl immobilized on agarose and sulphonyl immobilized on agarose, MonoS, MiniS, Source 15S, 30S, SP SEPHAROSE™, CM SEPHAROSE™, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS SP, Spherodex LS SP, DOWEX Fine Mesh Strong Acid Cation Resin, DOWEX MAC-3, Matrex Cellufine C500, Matrex Cellufine C200, Fractogel EMD SO3-, Fractogel EMD SE, Fractogel EMD COO—, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE(52, 53), P11, Express-Ion C and Express-Ion S, or any combination thereof.

In some embodiments, the chromatography comprises a AEX resin selected from POROS HQ, POROS XQ, Q SEPHAROSE™ Fast Flow, DEAE SEPHAROSE™ Fast Flow, SARTOBIND® Q, ANX SEPHAROSE™ 4 Fast Flow (high sub), Q SEPHAROSE™ XL, Q SEPHAROSE™ big beads, DEAE Sephadex A-25, DEAE Sephadex A-50, QAE Sephadex A-25, QAE Sephadex A-50, Q SEPHAROSE™ high performance, Q SEPHAROSE™ XL, Sourse 15Q, Sourse 30Q, Resourse Q, Capto Q, Capto DEAE, Mono Q, Toyopearl Super Q, Toyopearl DEAE, Toyopearl QAE, Toyopearl Q, Toyopearl GigaCap Q, TS gel SuperQ, TS gel DEAE, Fractogel EMD TMAE, Fractogel EMD TMAE HiCap, Fractogel EMD DEAE, Fractogel EMD DMAE, Macroprep High Q, Macro-prep-DEAE, Unosphere Q, Nuvia Q, PORGS PI, DEAE Ceramic HyperD, Q Ceramic HyperD, or any combination thereof.

In some embodiments, the protein is selected from an antibody or an antibody fragment, a fusion protein, a naturally-occurring protein, a chimeric protein, or any combination thereof. In some embodiments, the antibody is an isotype selected from IgM, IgA, IgE, IgD, and IgG. In some embodiments, the IgG antibody is selected from IgG1, IgG2, IgG3, and IgG4.

In some embodiments, the chromatography inactivates viruses. In some embodiments, the mixture has been isolated by subjecting a starting mixture an affinity chromatography selected from protein A affinity chromatography and protein G affinity chromatography. In some embodiments, the starting mixture is selected from a harvested cell culture fluid, a cell culture supernatant, a conditioned cell culture supernatant, a cell lysate, and a clarified bulk. In some embodiments, the starting is derived from a mammalian cell culture. In some embodiments, the starting mammalian cell culture is derived from Chinese hamster ovary (CHO) cells.

DETAILED DESCRIPTION OF THE DISCLOSURE

Figure 1:
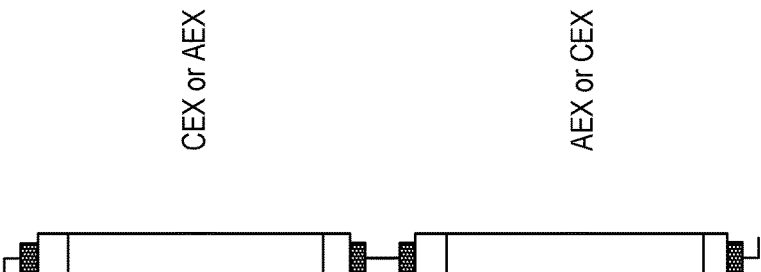
FIG. 1 shows a diagram of combined CEX-AEX or AEX-CEX polishing. The outlet of column 1 is directly connected to the inlet of column 2. No automation, engineering control, or adjustments are present or are made between these two columns.

The present disclosure provides a highly effective approach to remove contaminants during protein purification using affinity chromatography. Specifically, the approach uses cation exchange chromatography (CEX) and anion exchange chromatography (CEX) in tandem, either in AEX-CEX or CEX-AEX order. In some embodiments, the AEX and CEX have no adjustments made to the pH or the conductivity of the buffer between the AEX and CEX, or CEX and AEX. Another feature of the disclosure is that the column conditions of the AEX and CEX are processed together and operated as a single unit, which greatly reduces process cost, process operation time, and the process skid footprint.

As shown in the working examples, the approach is effective at removing unwanted contaminants in a mixture for proteins of interest with a wide range of isoelectric points. Use of such an AEX-CEX system allows for improving the process for both CEX and AEX simultaneously. In certain embodiments, the present disclosure provides a method of purifying a protein of interest from a mixture which comprises the protein of interest and one or more contaminants (e.g., host cell proteins, DNA, residual protein A, etc), wherein the CEX and AEX are operated in flow-through mode and the protein of interest does not strongly bind to either the CEX or AEX. Use of such a system allows for very high throughput wherein the CEX and AEX are used to remove unwanted contaminants from the mixture.

In certain embodiments, the present disclosure provides a method of purifying a protein of interest from a mixture which comprises the protein of interest and one or more contaminants. Possible contaminants include host cell proteins (HCP), high molecular weight species (HMWs), low molecular weight species (LMWs), DNA, and/or residual Protein A from previous Protein A capture step (rPA). The present disclosure also provides a method of reducing a buffer-transition post-loading peak, wherein the chromatographic process is disrupted when transitioning from the loading step to the post-loading chase buffer to chase the mixture through the column.

In certain embodiments, the present disclosure provides a method of purifying an antibody. In certain embodiments, the mixture is derived from harvested cell culture fluid, cell culture supernatant, cell lysate, and clarified bulk.

I. Terms

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, the term "protein of interest" is used in its broadest sense to include any protein (either natural or recombinant), present in a mixture, for which purification is desired. Such proteins of interest include, without limitation, enzymes, hormones, growth factors, cytokines, immunoglobulins (e.g., antibodies), and/or any fusion proteins.

The term "clarification" refers to the process of removing particulates. Clarification can lower the burden on subsequent chromatography (for example, AEX or CEX) during a purification process. In some examples, clarification is a method of removing colloids, lipids, DNA-RNA, residual cells, and other particles from cell culture. Filtration may also be used, and can include depth filters. "Clarified bulk" refers to a mixture that has been subjected to the process of clarification.

The term "virus inactivation" refers to a process of removing infective viral contaminants from a mixture. There are currently many different methods for inactivating contagious pathogenic viruses, including, e.g., heat-inactivation, solvent/detergent (S/D) inactivation, pH inactivation, chemical inactivation, and/or ultraviolet irradiation inactivation.

The term "chromatography" refers to any kind of technique which separates a protein of interest (e.g., an antibody) from other molecules (e.g., contaminants) present in a mixture. Usually, the protein of interest is separated from other molecules (e.g., contaminants) as a result of differences in rates at which the individual molecules of the mixture migrate through a stationary medium under the influence of a moving phase, or in bind and elute processes. The term "matrix" or "chromatography matrix" are used interchangeably herein and refer to any kind of sorbent, resin or solid phase which in a separation process separates a protein of interest (e.g., an Fc region containing protein such as an immunoglobulin) from other molecules present in a mixture. Non-limiting examples include particulate, monolithic or fibrous resins as well as membranes that can be put in columns or cartridges. Examples of materials for forming the matrix include polysaccharides (such as agarose and cellulose); and other mechanically stable matrices such as silica (e.g. controlled pore glass), poly(styrenedivinyl)benzene, polyacrylamide, ceramic particles and derivatives of any of the above. Examples for typical matrix types suitable for the method of the present disclosure are cation exchange resins, affinity resins, anion exchange resins or mixed mode resins. A "ligand" is a functional group that is attached to the chromatography matrix and that determines the binding properties of the matrix. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Some preferred ligands that can be used herein include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as N5N diethylamino or DEAE; hydrophobic interaction groups, such as phenyl, butyl, propyl, hexyl; and affinity groups, such as Protein A, Protein G, and Protein L. In order that the present disclosure may be more readily understood, certain terms are first defined. As used in this application, except as otherwise expressly provided herein, each of the following terms shall have the meaning set forth below. Additional definitions are set forth throughout the application.

The term "affinity chromatography" refers to a protein separation technique in which a protein of interest (e.g., an Fc region containing protein of interest or antibody) is specifically bound to a ligand which is specific for the protein of interest. Such a ligand is generally referred to as a biospecific ligand. In some embodiments, the biospecific ligand (e.g., Protein A or a functional variant thereof) is covalently attached to a chromatography matrix material and is accessible to the protein of interest in solution as the solution contacts the chromatography matrix. The protein of interest generally retains its specific binding affinity for the biospecific ligand during the chromatographic steps, while other solutes and/or proteins in the mixture do not bind appreciably or specifically to the ligand. Binding of the protein of interest to the immobilized ligand allows contaminating proteins or protein impurities to be passed through the chromatography matrix while the protein of interest remains specifically bound to the immobilized ligand on the solid phase material. The specifically bound protein of interest is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g., antibody. However, in various methods according to the present disclosure, Protein A is used as a ligand for an Fc region containing a target protein. The conditions for elution from the biospecific ligand (e.g., Protein A) of the target protein (e.g., an Fc region containing protein) can be readily determined by one of ordinary skill in the art. In some embodiments, Protein G or Protein L or a functional variant thereof may be used as a biospecific ligand. In some embodiments, a biospecific ligand such as Protein A is used at a pH range of 5-9 for binding to an Fc region containing protein, washing or re-equilibrating the biospecific ligand/target protein conjugate, followed by elution with a buffer having pH about or below 4 which contains at least one salt.

The terms "purifying," "separating," or "isolating," as used interchangeably herein, refer to increasing the degree of purity of a protein of interest from a composition or sample comprising the protein of interest and one or more impurities. Typically, the degree of purity of the protein of interest is increased by removing (completely or partially) at least one impurity from the composition.

The term "buffer" as used herein, refers to a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. Traditional buffer components include, but are not limited to, organic and inorganic salts, acids and bases.

The term "conductivity" as used herein, refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm), and can be measured using a conductivity meter.

The term "chromatography column" or "column" in connection with chromatography as used herein, refers to a container, frequently in the form of a cylinder or a hollow pillar which is filled with the chromatography matrix or resin. The chromatography matrix or resin is the material which provides the physical and/or chemical properties that are employed for purification.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange (CEX), anion exchange (AEX), and mixed mode chromatography.

A "cation exchange resin" or "cation exchange membrane" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP SEPHAROSE® Fast Flow, SP SEPHAROSE® High Performance, Capto S, Capto SP ImpRes from GE Healthcare, TOYOPEARL® SP-650S and SP-650M from Tosoh, MACRO-PREP® High S from BioRad, Ceramic HyperD S, TRISACRYL® M and LS SP and Spherodex LS SP from Pall Technologies); a sulfoethyl based group (e.g., FRAC-TOGEL® SE, from EMD, POROS® S-10 and S-20 from Applied Biosystems); a sulphopropyl based group (e.g., TSK Gel SP 5PW and SP-5PW-HR from Tosoh, POROS® HS-20, HS 50, and POROS® XS from Life Technologies); a sulfoisobutyl based group (e.g., FRACTOGEL® EMD $SO_3^-$ from EMD); a sulfoxyethyl based group (e.g., SE52, SE53 and Express-Ion S from Whatman), a carboxymethyl based group (e.g., CM SEPHAROSE® Fast Flow from GE Healthcare, Hydrocell CM from Biochrom Labs Inc., MACRO-PREP® CM from BioRad, Ceramic HyperD CM, TRISACRYL® M CM, TRISACRYL® LS CM, from Pall Technologies, Matrx CELLUFINE® C500 and C200 from Millipore, CM52, CM32, CM23 and Express-Ion C from Whatman, TOYOPEARL® CM-650S, CM-650M and CM-650C from Tosoh); sulfonic and carboxylic acid based groups (e.g., BAKERBOND® Carboxy-Sulfon from J. T. Baker); a carboxylic acid based group (e.g., WP CBX from J. T Baker, DOWEX®. MAC-3 from Dow Liquid Separations, AMBERLITE® Weak Cation Exchangers, DOWEX® Weak Cation Exchanger, and DIAION® Weak Cation Exchangers from Sigma-Aldrich and FRACTOGEL® EMD COO— from EMD); a sulfonic acid based group (e.g., Hydrocell SP from Biochrom Labs Inc., DOWEX® Fine Mesh Strong Acid Cation Resin from Dow Liquid Separations, UNOsphere S, WP Sulfonic from J. T. Baker, SAR-TOBIND® S membrane from Sartorius, AMBERLITE® Strong Cation Exchangers, DOWEX® Strong Cation and DIAION® Strong Cation Exchanger from Sigma-Aldrich); or a orthophosphate based group (e.g., P11 from Whatman). Other cation exchange resins include carboxy-methyl-cellulose, BAKERBOND ABX™, Ceramic HyperD Z, Matrex Cellufine C500, Matrex Cellufine C200.

An "anion exchange resin" or "anion exchange membrane" refers to a solid phase which is positively charged, thus having one or more positively charged ligands attached thereto. Any positively charged ligand attached to the solid phase suitable to form the anionic exchange resin can be used, such as quaternary amino groups. Commercially available anion exchange resins include DEAE cellulose, POROS® PI 20, PI 50, HQ 10, HQ 20, HQ 50, D 50 from Applied Biosystems, SARTOBIND® Q from Sartorius, MonoQ, MiniQ, Source 15Q and 30Q, Q, DEAE and ANX SEPHAROSE® Fast Flow, Q SEPHAROSE® High Performance, QAE SEPHADEX® and FAST Q SEPHAROSE® (GE Healthcare), WP PEI, WP DEAM, WP QUAT from J. T. Baker, Hydrocell DEAE and Hydrocell QA from Biochrom Labs Inc., UNOsphere Q, MACRO-PREP®. DEAE and MACRO-PREP® High Q from Biorad, Ceramic HyperD Q, ceramic HyperD DEAE, TRISACRYL® M and LS DEAE, Spherodex LS DEAE, QMA SPHEROSIL® LS, QMA SPHEROSIL®. M and MUSTANG® Q from Pall Technologies, DOWEX® Fine Mesh Strong Base Type I and Type II Anion Resins and DOWEX® MONOSPHER E 77, weak base anion from Dow Liquid Separations, INTER-CEPT® Q membrane, Matrex CELLUFINE® A200, A500, Q500, and Q800, from Millipore, FRACTOGEL® EMD TMAE, FRACTOGEL® EMD DEAE and FRACTOGEL® EMD DMAE from EMD, AMBERLITE® weak strong anion exchangers type I and II, DOWEX® weak and strong anion exchangers type I and II, DIAION® weak and strong anion exchangers type I and II, DUOLITE® from Sigma-Aldrich, TSK gel Q and DEAE 5PW and 5PW-HR, TOYO-PEARL® SuperQ-6505, 650M and 650C, QAE-550C and 650S, DEAE-650M and 650C from Tosoh, QA52, DE23, DE32, DE51, DE52, DE53, Express-Ion D or Express-Ion Q from Whatman, and SARTOBIND® Q (Sartorius Corporation, New York, USA). Other anion exchange resins include POROS XQ, SARTOBIND® Q, Q SEPHAROSE™ XL, Q SEPHAROSE™ big beads, DEAE Sephadex A-25, DEAE Sephadex A-50, QAE Sephadex A-25, QAE Sephadex A-50, Q SEPHAROSE™ high performance, Q SEPHAROSE™ XL, Resource Q, Capto Q, Capto DEAE, Toyopearl GigaCap Q, Fractogel EMD TMAE HiCap, Nuvia Q, or PORGS PI.

The term "flow-through" or "flow-through mode" as used herein refers to the general purification approach wherein contaminants are removed from a mixture during chromatography because they are retained by a chromatographic process, usually bound to a resin in a column. A protein of interest is purified because it does not bind (or it binds less strongly than contaminants) to a chromatographic medium, usually a resin in a column, and instead flows through to be collected. After elution of the protein of interest, the impurities bound to the column must be "stripped", or removed from the column, so that the column can then be regenerated for another chromatographic run. This approach differs from "bind-and-elute" or "bind-and-elute mode" wherein the target protein of interest is retained on a column and impurities flow through the column. This process then involves specific elution of the protein of interest using different column conditions that interfere with the binding of the protein of interest to the chromatographic medium, usually a resin in a column.

As used herein the term "contaminant" is used in its broadest sense to cover any undesired component or compound within a mixture. In cell cultures, cell lysates, or clarified bulk (e.g., clarified cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants. In certain embodiments, the contaminant precipitate is separated from the cell culture using another means, such as centrifugation, sterile filtration, depth filtration and tangential flow filtration.

The term "antibody" refers, in some embodiments, to a protein comprising at least two heavy (H) chains and two light (L) chains inter-connected by disulfide bonds. Each heavy chain is comprised of a heavy chain variable region (abbreviated herein as VH) and a heavy chain constant region (abbreviated herein as CH). In some antibodies, e.g., naturally-occurring IgG antibodies, the heavy chain constant region is comprised of a hinge and three domains, CH1, CH2 and CH3. In some antibodies, e.g., naturally-occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. A heavy chain may have the C-terminal lysine or not. The term "antibody" can include a bispecific antibody or a multispecific antibody.

An "IgG antibody", e.g., a human IgG1, IgG2, IgG3 and IgG4 antibody, as used herein has, in some embodiments, the structure of a naturally-occurring IgG antibody, i.e., it has the same number of heavy and light chains and disulfide bonds as a naturally-occurring IgG antibody of the same subclass. For example, an IgG1, IgG2, IgG3 or IgG4 antibody may consist of two heavy chains (HCs) and two light chains (LCs), wherein the two HCs and LCs are linked by the same number and location of disulfide bridges that occur in naturally-occurring IgG1, IgG2, IgG3 and IgG4 antibodies, respectively (unless the antibody has been mutated to modify the disulfide bridges).

An immunoglobulin can be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally-occurring and non-naturally-occurring antibodies; monoclonal and poly-clonal antibodies; chimeric and humanized antibodies; human and nonhuman antibodies and wholly synthetic antibodies.

The term "antigen-binding portion" of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment (fragment from papain cleavage) or a similar monovalent fragment consisting of the VL, VH, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR) and (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences.

The term "isoelectric point" or "pI" of a protein refers to a measure of the pH of a solution in which a protein carries no net charge. When a protein is found at a pH equivalent to its pI, it will carry globally neutral net electric charge. Proteins that have a pI lower than the pH of its solution will carry a net negative charge. Likewise, proteins that have a pI higher than the pH of its solution will carry a net positive charge.

The term "loading buffer" refers to the buffer used to prepare and load a mixture or sample into the chromatography unit.

The term "chase buffer" refers to the buffer used subsequent to the loading buffer, in order to drive the mixture or sample through the chromatographic process.

The term "in-line adjustment" refers to any addition of a mixture or solution between the AEX and CEX or between the CEX and AEX in order to adjust the solution conditions or composition between chromatography steps. In some embodiments, the AEX-CEX order is used and no pH and/or conductivity adjustments are made after the mixture has left the AEX but before it has entered the CEX. In other embodiments, the CEX-AEX order is used and no pH or conductivity adjustments are made after the mixture has left the CEX but before it has entered the AEX.

The term "HMW Species" refers to any one or more unwanted proteins present in a mixture. High molecular weight species can include dimers, trimers, tetramers, or other multimers. These species are often considered product related impurities, and can either be covalently or non-covalently linked, and can also, for example, consist of misfolded monomers in which hydrophobic amino acid residues are exposed to a polar solvent, and can cause aggregation.

The term "LMW Species" refers to any one or more unwanted species present in a mixture. Low molecular weight species are often considered product related impurities, and can include clipped species, or half molecules for compounds intended to be dimeric (such as monoclonal antibodies).

The term "Host Cell Proteins" or HCP refers to the undesirable proteins generated by a host cell unrelated to the production of the intended protein of interest. Undesirable host cell proteins can be secreted into the upstream cell culture supernatant. Undesirable host cell proteins can also be released during cell lysis. The cells used for upstream cell culture require proteins for growth, transcription, and protein synthesis, and these unrelated proteins are undesirable in a final drug product.

The term "residual Protein A" (rPA) refers to a protein originally discovered in the cell wall of the bacterial *Staphylococcus aureus*. Protein A is approximately 42 kDa and binds very strongly to the Fc portion of an immunoglobulin, and its use in the purification of antibodies is well known in the art. Protein A has been extensively used in the art for purification. (Boyle et al., 1993; Hou et al. 1991). When applied to Protein A, the term "residual", or "rPA" refers to any remaining Protein A present in a mixture due its use in purification of a protein of interest or an antibody further upstream in a manufacturing process.

The term "buffer transition peak" refers to an unwanted chromatographic elution due to changing conditions during chromatography. In some embodiments, the first buffer is a loading buffer used at the outset of chromatography. In some embodiments, the second buffer is a chase buffer used to chase the initially loaded mixture through the chromatography process. The buffer transition peak can appear during the transition from the use of the loading buffer to the use of the chase buffer. In other embodiments, the buffer transition peak can be produced due to the difference between a first buffer, e.g., loading buffer, and the second buffer, e.g., chase buffer.

Various aspects of the disclosure are described in further detail in the following subsections.

II. Methods of Purification

The present disclosure is directed to a method purifying a protein of interest from a mixture, the method comprising performing a combined cation exchange chromatography (CEX) and anion exchange chromatography (AEX) or a combined AEX and CEX ("combined chromatography") in flow-through mode under an operating condition wherein no change to the operating condition was added between the AEX and the CEX (or CEX and AEX). No change to the operating condition between the AEX and the CEX (or CEX and AEX) includes, but is not limited to, no automation, engineering control, and/or in-line adjustment. In order to avoid adding any changes between the AEX and the CEX (or CEX and AEX) processes, in some embodiments, the AEX and the CEX (or CEX and AEX) can be directly connected to each other as shown in FIG. 1. In other embodiments, the AEX and the CEX (or CEX and AEX) are not directly connected to each other, but the operating conditions (e.g., pH and/or conductivity) between the AEX and the CEX (or CEX and AEX) are not changed, i.e., maintained the same way. The operating condition can be changed through the use of buffers during the chromatography. In some embodiments, the chromatography comprises a loading buffer and/or a chase buffer.

In some embodiments, the combined AEX and CEX (or CEX and AEX) chromatography columns are loaded to about 50 g/L resin, about 60 g/L resin, about 70 g/L resin, about 80 g/L resin, about 90 g/L resin, about 100g/L resin, about 110 g/L resin, about 120 g/L resin, about 130 g/L resin, about 140 g/L resin, about 150g/L resin, about 160 g/L resin, about 170 g/L resin, about 180 g/L resin, about 190 g/L resin, about 200 g/L resin, about 210 g/L resin, about 220 g/L resin, about 230 g/L resin, about 240 g/L resin, about 250g/L resin, about 260 g/L resin, about 270 g/L resin, about 280 g/L resin, about 290 g/L resin, about 300 g/L resin, about 310 g/L resin, about 320 g/L resin, about 330 g/L resin, about 340 g/L resin, about 350g/L resin, about 360 g/L resin, about 370 g/L resin, about 380 g/L resin, about 390 g/L resin, about 400 g/L resin, about 410 g/L resin, about 420 g/L resin, about 430 g/L resin, about 440 g/L resin, about 450g/L resin, about 460 g/L resin, about 470 g/L resin, about 480 g/L resin, about 490 g/L resin, about 500 g/L resin, about 510 g/L resin, about 520 g/L resin, about 530 g/L resin, about 540 g/L resin, about 550g/L resin, about 560 g/L resin, about 570 g/L resin, about 580 g/L resin, about 590 g/L resin, or about 600 g/L resin. In some embodiments, combined AEX and CEX (or CEX and AEX) chromatography columns are loaded to about 300 g/L resin.

In some embodiments, proteins of interest in the present disclosure can carry a charge when placed in a buffer solution if the pH of the buffer differs from the measured pI of the protein. When a protein of interest is found at a pH equivalent to its pI, it will carry globally neutral net charge. Proteins of interest that have a pI lower than the pH of the solution will carry a net negative charge. Likewise, proteins of interest that have a pI higher than the pH of the solution will carry a net positive charge.

It is well known that buffer pH and ionic strength are crucial for all forms of ion exchange chromatography and thus it is best to readjust buffer pH after salt concentration has been adjusted and ensure that buffer counterions are compatible. It is known that buffer counterions should have the same charge as the resins. Especially when two opposite chromatography steps (e.g., AEX and CEX) are combined together, it has been expected that the pH and/or conductivity for AEX and CEX would be adjusted in between.

The present methods are based on the surprising discovery that certain operating conditions for the combined AEX and CEX (or CEX and AEX) chromatography, e.g., in flow through mode, can be maintained without any adjustments between the AEX and CEX (or vice versa).

In some embodiments, the operating conditions for the combined AEX and CEX (or CEX and AEX) are set prior to the first chromatography and are maintained throughout based on the pI of the protein of interest. In other embodiments, the operating conditions are set based on two different pIs, e.g., mid to high pI and low pI. In some embodiments the operating conditions are set for protein of interest with mid to high pI, e.g., pI≥about 6.5, and for protein of interest with low pI, e.g., pI<6.5.

In some embodiments, a protein of interest has a mid to high pI, which is higher than about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the protein of interest having a mid to high pI has a pI≥(higher than) 6.5 and a pI≤(lower than) about 12.0, about 11.9, about 11.8, about 11.7, about 11.6, about 11.5, about 11.4, about 11.3, about 11.2, about 11.1, about 11.0, about 10.9, about 10.8, about 10.8, about 10.7, about 10.6, about 10.5, about 10.4, about 10.3, about 10.2, about 10.1, or about 10.0. In some embodiments, the protein of interest having a mid to high pI has a pI≥(higher than) 6.5 and a pI≤(lower than) about 10.0, about 9.9, about 9.8, about 9.7, about 9.6, about 9.5, about 9.4, about 9.3, about 9.2, about 9.1, about 9.0, about 8.9, about 8.8, about 8.7, about 8.6, about 8.5, about 8.4, about 8.3, about 8.2, about 8.1, or about 8.0. In some embodiments, the protein of interest having a mid to high pI has a pI between about 7.0 and about 11.0, between about 7.0 and about 10.9, between about 7.1 and about 10.9, between about 7.2 and about 10.9, between about 7.2 and about 10.8, between about 7.3 and about 10.8, between about 7.3 and about 10.7, between about 7.4 and about 10.7, between about 7.4 and about 10.6, between about 7.5 and about 10.6, between about 7.5 and about 10.5, between about 7.6 and about 10.5, between about 7.6 and about 10.4, between about 7.7 and about 10.4, between about 7.7 and about 10.3, between about 7.8 and about 10.3, between about 7.8 and about 10.2, between about 7.9 and about 10.2, between about 7.9 and about 10.1, between about 8.0 and about 10.1, between about 8.0 and about 10.0, between about 8.1 and about 10.0, between about 8.1 and about 9.9, between about 8.2 and about 9.9, between about 8.2 and about 9.8, between about 8.3 and about 9.8, between about 8.3 and about 9.7, between about 8.4 and about 9.7, between about 8.4 and about 9.6, between about 8.5 and about 9.6, or between about 8.5 and about 9.5. In other embodiments, the protein of interest has a pI of about 6.5, about 7.0, about 7.5, about 8.0, about 8.0, about 8.5, about 9.0, about 9.5, about 10.0, about 10.5, or about 11.0.

In some embodiments, the protein of interest with a mid to high pI has a pI between about 7.0 and about 8.0, e.g., of about 7.6. In other embodiments, the protein of interest with a mid to high pI has a pI between about 8.0 and about 9.0, e.g., of about 8.4. In some embodiments, the protein of interest with a mid to high pI has a pI between 8.5 and between 9.5, e.g., of about 8.9. In other embodiments, the protein of interest with a mid to high pI has a pI between about 9.0 to about 10.0.

In some embodiments, the protein of interest has a low pI, which is lower than about 6.5, about 6.4, about 6.3, about 6.2, about 6.1, about 6.0, about 5.9, about 5.8, about 5.7, about 5.6, about 5.5, about 5.4, about 5.3, about 5.2, about 5.1, or about 5.0. In some embodiments, a protein of interest with a low pI has a pI lower than 6.5 and higher than about 1.0, about 2.0, about 3.0, about 4.0, about 5.0, or about 5.5. In some embodiments, the protein of interest with a low pI has a pI between about 1.0 and about 6.5, between about 1.5 and about 6.5, between about 2.0 and about 6.5, between about 2.5 and about 6.5, between about 2.5 and about 6.0, between about 3.0 and about 6.5, between about 3.0 and about 6.0, between about 3.0 and about 5.5, between about 3.5 and about 5.5, or between about 3.5 and about 5.0.

In some embodiments, the protein of interest has an isoelectric point (pI) between about 4.8 and about 6.5, between about 4.9 and about 6.5, between about 4.9 and about 6.4, between about 5.0 and about 6.4, between about 5.0 and about 6.3, between about 5.1 and about 6.3, between about 5.1 and about 6.2, between about 5.2 and about 6.2, between about 5.2 and about 6.4, or between about 5.3 and about 6.4. In other embodiments, the protein of interest has a pI between about 5.0 and about 6.0.

In certain embodiments, at least one of the operating conditions (e.g., pH) for the proteins of interest with mid to high pIs and the proteins of interest with low pI can be the same. In other embodiments, the pH of the loading buffer and/or the chase buffer can be the same for the protein of interest with mid to high pI and the protein of interest with low pI. In some embodiments, the pH of the loading buffer and/or the chase buffer can be different for the protein of interest with mid to high pI and the protein of interest with low pI.

In some embodiments, the loading buffer for the combined chromatography has a pH≥(higher than) about 5.0, about 5.5, about 6.0, about 6.5, about 7.0, about 7.5, about 8.0, about 8.5, about 9.0, about 9.5, or about 10.0. In some embodiments, the loading buffer has a pH higher than about 5.0, about 5.1, about 5.2, about 5.3, about 5.4, about 5.5, about 5.6, about 5.7, or about 5.8. about 5.9, about 6.0, about 6.1, about 6.2, about 6.3, about 6.4, about 6.5, about 6.6, about 6.7, or about 6.8. about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, or about 9.8. about 9.9, or about 10.0. In some embodiments, the loading buffer has a pH of about 5.0, about 5.1, about 5.2, about 5.3, about 5.4, about 5.5, about 5.6, about 5.7, or about 5.8. about 5.9, about 6.0, about 6.1, about 6.2, about 6.3, about 6.4, about 6.5, about 6.6, about 6.7, or about 6.8. about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8. about 9.9, or about 10.0.

In some embodiments, the loading buffer for the combined chromatography has a pH between about 6.0 and about 11.0, between about 6.5 and about 11.0, between about 7.0 and about 10.5, between about 7.0 and about 10.0, between about 7.0 and about 9.5, between about 7.0 and about 9.0, between about 7.0 and about 8.5, between about 7.0 and about 8.0, between about 7.0 and about 7.5, between about 7.0 and 7.4, between about 7.1 and about 7.4, between about 7.2 and about 7.4.

In some embodiments, the loading buffer for the combined chromatography has a pH of about 6.5, about 7.0, about 7.2, about 7.4, about 7.6, about 7.8, about 8.0, about 8.2, about 8.4, about 8.6, about 8.8, about 9.0, about 9.2, about 9.4, about 9.6, about 9.8, about 10.0, about 10.5, about 11.0, or about 11.5.

In some embodiments, a protein of interest has a mid to high pI between about 7.0 and about 8.0, (e.g., of about 7.6), and the loading buffer for the protein has a pH between about 7.0 and about 8.0, e.g., of about 7.4.

In other embodiments, a protein of interest has a mid to high pI between about 8.0 and about 9.0, (e.g., of about 8.4), and the loading buffer of the protein has a pH between about 7.0 and about 8.0, e.g., of about 7.2.

In some embodiments, a protein of interest has a mid to high pI between 8.5 and between 9.5 (e.g., of about 8.9), and the loading buffer for the protein has a pH between about 7.5 and about 8.5, e.g., of about 8.0.

In other embodiments, a protein of interest has a mid to high pI between about 9.0 to about 10.0, (e.g., of about 9.2), and the loading buffer for the protein has a pH between about 7.0 and about 8.0, e.g., of about 7.2.

In other embodiments, the protein of interest has a low pI between about 5.0 and about 6.0, e.g., of about 5.8, and the loading buffer for the protein has a pH between about 6.5 and about 7.5, e.g., of about 7.0.

In other embodiments, the loading buffer and the chase buffer for the combined chromatography has the same operating conditions. In certain embodiments, the buffer conditions, e.g., pH are maintained the same between the loading buffer and the chase buffer. In other embodiments, the buffer conditions between the loading buffer and the chase buffer are different.

In some embodiments, the chase buffer has a pH >(higher than) about 5.0, about 5.5, about 6.0, about 6.5, about 7.0, about 7.5, about 8.0, about 8.5, about 9.0, about 9.5, or about 10.0. In other embodiments, the chase buffer has a pH >(higher than) about 5.0, about 5.1, about 5.2, about 5.3, about 5.4, about 5.5, about 5.6, about 5.7, or about 5.8. about 5.9, about 6.0, about 6.1, about 6.2, about 6.3, about 6.4, about 6.5, about 6.6, about 6.7, or about 6.8. about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8. about 9.9, about 10.0, about 10.1, about 10.2, about 10.3, about 10.4, about 10.5, about 10.6, about 10.7, about 10.8, about 10.9, or about 11.0.

In some embodiments, the chase buffer has a pH of about 5.0, about 5.1, about 5.2, about 5.3, about 5.4, about 5.5, about 5.6, about 5.7, or about 5.8. about 5.9, about 6.0, about 6.1, about 6.2, about 6.3, about 6.4, about 6.5, about 6.6, about 6.7, or about 6.8. about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, or about 11.0.

In some embodiments, the chase buffer has a pH between about 6.0 and about 11.0, between about 6.5 and about 11.0, between about 7.0 and about 10.5, between about 7.0 and about 10.0, between about 7.0 and about 9.5, between about 7.0 and about 9.0, between about 7.0 and about 8.5, between about 7.0 and about 8.0, between about 7.0 and about 7.5, between about 7.0 and 7.4, between about 7.1 and about 7.4, or between about 7.2 and about 7.4. In some embodiments, the chase buffer has a pH of about 6.5, about 7.0, about 7.2, about 7.4, about 7.6, about 7.8, about 8.0, about 8.2, about 8.4, about 8.6, about 8.8, about 9.0, about 9.2, about 9.4, about 9.6, about 9.8, about 10.0, about 10.5, about 11.0, or about 11.5. In some embodiments, the chase buffer has a pH between about 6.0 and about 11.0. between about 6.5 and about 10.0, between about 7.0 and about 11.0, between about 7.0 and about 10.0, between about 7.0 and about 9.0, between about 7.0 and about 8.0, between about 7.0 and about 8.5, between about 7.0 and about 9.5, between about 6.5 and about 8.5, or between about 6.5 and about 7.5.

In some embodiments, the protein of interest has a pI between about 7.0 and about 8.0, e.g., of about 7.6, and the loading buffer and the chase buffer for the protein have the same pH between about 7.0 and about 8.0, e.g., of about 7.4.

In other embodiments, the protein of interest has a pI between about 8.0 and about 9.0, e.g., of about 8.4 and the loading buffer and the chase buffer for the protein have the same pH between about 7.0 and about 8.0, e.g., of about 7.2.

In some embodiments, the protein of interest has a pI between 8.5 and about 9.5, e.g., of about 8.9, and the loading buffer and the chase buffer for the protein have the same pH between about 7.5 and about 8.5, e.g., of about 8.0.

In other embodiments, the protein of interest has a pI between about 9.0 to about 10.0, e.g., of about 9.2, and the loading buffer and the chase buffer for the protein have the same pH between about 7.0 and about 8.0, e.g., of about 7.2.

In other embodiments, the protein of interest has a pI between about 5.0 and about 6.0, e.g., of about 5.8, and the loading buffer and the chase buffer for the protein have the same pH between about 6.5 and about 7.5, e.g., of about 7.0.

In other embodiments, the operating conditions for the protein of interest with mid and high pI and the protein of interest with low pI can be different. In some embodiments, the conductivity for the protein of interest with mid and high pI and the protein of interest with low pI is different. In some embodiments, the conductivity for the protein with low pI is higher than the conductivity for the protein with mid to high pI.

In some embodiments, the conductivity for a loading buffer and/or a chase buffer of the protein of interest with mid to high pI is between about 0.1 mS/cm to about 9.0 mS/cm, between about 0.5 mS/cm to about 9.0 mS/cm, between about 1.0 mS/cm to about 9.0 mS/cm, between about 2.0 mS/cm to about 8.0 mS/cm, between about 2.0 mS/cm to about 7.0 mS/cm, between about 2.0 mS/cm to about 8.5 mS/cm, between about 2.0 mS/cm to about 7.5 mS/cm, or between about 2.5 mS/cm to about 7.0 mS/cm. In some embodiments, the conductivity for a loading buffer and/or a chase buffer of the protein of interest with mid to high pI is between about 2.5 mS/cm to about 7.0 mS/cm.

In some embodiments, the conductivity for a loading buffer and/or a chase buffer of the protein of interest with mid to high pI is about 0.1 mS/cm, about 0.5 mS/cm, about 1.0 mS/cm, about 1.5 mS/cm, about 2.0 mS/cm, about 2.5 mS/cm, about 3.0 mS/cm, about 3.5 mS/cm, about 4.0 mS/cm, about 4.5 mS/cm, about 5.0 mS/cm, about 5.5 mS/cm, about 6.0 mS/cm, about 6.5 mS/cm, about 7.0 mS/cm, about 7.5 mS/cm, about 8.0 mS/cm, about 8.5 mS/cm, or about 9.0 mS/cm.

In some embodiments, the loading buffer and/or the chase buffer for the protein of interest with mid to high pI has a pH of between about 7.0 and about 8.0 and a conductivity between about 2.0 mS/cm and about 7.0 mS/cm, e.g., about 2.0 mS/cm, about 2.5 mS/cm, about 2.7 mS/cm, about 3.0 mS/cm, about 3.2 mS/cm, about 3.5 mS/cm, about 4.0 mS/cm, about 4.5 mS/cm, about 5.0 mS/cm, about 5.5 mS/cm, about 6.0 mS/cm, about 6.5 mS/cm, about 6.8 mS/cm, or about 7.0 mS/cm.

In some embodiments, the conductivity for a loading buffer and/or a chase buffer of the protein of interest with low pI is between about 6.0 mS/cm to about 15.0 mS/cm, between about 6.5 mS/cm to about 15 mS/cm, between about 7.0 mS/cm to about 14.0 mS/cm, between about 8.0 mS/cm to about 13.0 mS/cm, about 8.0 mS/cm to about 12.0 mS/cm, or between about 9.0 mS/cm to about 12.0 mS/cm.

In some embodiments, the conductivity for a loading buffer and/or a chase buffer of the protein of interest with low pI is about 6.0 mS/cm, about 6.1 mS/cm, about 6.2 mS/cm, about 6.3 mS/cm, about 6.4 mS/cm, about 6.5 mS/cm, about 6.6 mS/cm, about 6.7 mS/cm, about 6.8 mS/cm, about 6.9 mS/cm, about 7.0 mS/cm, about 7.1 mS/cm, about 7.2 mS/cm, about 7.3 mS/cm, about 7.4 mS/cm, about 7.5 mS/cm, about 7.6 mS/cm, about 7.7 mS/cm, about 7.8 mS/cm, about 7.9 mS/cm, about 8.0 mS/cm, about 8.1 mS/cm, about 8.2 mS/cm, about 8.3 mS/cm, about 8.4 mS/cm, about 8.5 mS/cm, about 8.6 mS/cm, about 8.7 mS/cm, about 8.8 mS/cm, about 8.9 mS/cm, about 9.0 mS/cm, about 9.1 mS/cm, about 9.2 mS/cm, about 9.3 mS/cm, about 9.4 mS/cm, about 9.5 mS/cm, about 9.6 mS/cm, about 9.7 mS/cm, about 9.8 mS/cm, about 9.9 mS/cm, about 10.0 mS/cm, about 10.1 mS/cm, about 10.2 mS/cm, about 10.3 mS/cm, about 10.4 mS/cm, about 10.5 mS/cm, about 10.6 mS/cm, about 10.7 mS/cm, about 10.8 mS/cm, about 10.9 mS/cm, about 11.0 mS/cm, about 11.1 mS/cm, about 11.2 mS/cm, about 11.3 mS/cm, about 11.4 mS/cm, about 11.5 mS/cm, about 11.6 mS/cm, about 11.7 mS/cm, about 11.8 mS/cm, about 11.9 mS/cm about 12.0 mS/cm, about 12.1 mS/cm, about 12.2 mS/cm, about 12.3 mS/cm, about 12.4 mS/cm, about 12.5 mS/cm, about 12.6 mS/cm, about 12.7 mS/cm, about 12.8 mS/cm, about 12.9 mS/cm, about 13.0 mS/cm, about 13.1 mS/cm, about 13.2 mS/cm, about 13.3 mS/cm, about 13.4 mS/cm, about 13.5 mS/cm, about 13.6 mS/cm, about 13.7 mS/cm, about 13.8 mS/cm, about 13.9 mS/cm, about 14.0 mS/cm, about 14.1 mS/cm, about 14.2 mS/cm, about 14.3 mS/cm, about 14.4 mS/cm, about 14.5 mS/cm, about 14.6 mS/cm, about 14.7 mS/cm, about 14.8 mS/cm, about 14.9 mS/cm, or about 15.0 mS/cm.

In some embodiments, the loading buffer and/or the chase buffer for the protein of interest with low pI has a pH of between about 7.0 and about 8.0 and a conductivity between about 8.0 mS/cm and 13.0 mS/cm.

In some embodiments, the protein of interest has a pI between about 7.0 and about 8.0, e.g., of about 7.6, and the loading buffer and the chase buffer for the protein have the same pH between about 7.0 and about 8.0, e.g., of about 7.4, and have a conductivity between 3.0 mS/cm and 6.0 mS/cm, e.g., 3.2 mS/cm and 5.5 mS/cm, respectively.

In other embodiments, the protein of interest has a pI between about 8.0 and about 9.0, e.g., of about 8.4, and the loading buffer and the chase buffer for the protein have the same pH between about 7.0 and about 8.0, e.g., of about 7.2, and have a conductivity between 2.0 mS/cm and 4.0 mS/cm, e.g., 2.7 mS/cm and 3.0 mS/cm, respectively.

In some embodiments, the protein of interest has a pI between 8.5 and between 9.5, e.g., of about 8.9, and the loading buffer and the chase buffer for the protein have the same pH between about 7.5 and about 8.5, e.g., of about 8.0, and have a conductivity between 2.0 mS/cm and 5.0 mS/cm, e.g., 3.0 mS/cm and 4.5 mS/cm, respectively.

In other embodiments, the protein of interest has a pI between about 9.0 to about 10.0, e.g., of about 9.2, and the loading buffer and the chase buffer for the protein have the same pH between about 7.0 and about 8.0, e.g., of about 7.2, and have a conductivity between 6.0 mS/cm and 7.0 mS/cm, e.g., 6.8 mS/cm and 6.8 mS/cm, respectively.

In other embodiments, the protein of interest has a pI between about 5.0 and about 6.0, e.g., of about 5.8, and the loading buffer and the chase buffer for the protein have the same pH between about 6.5 and about 7.5, e.g., of about 7.0, and have a conductivity between 9.0 mS/cm and 12.0 mS/cm, e.g., 9.2 mS/cm and 12.0 mS/cm, respectively.

The methods disclosed herein (II and III) can be used to purify a protein of interest in a mixture containing contaminants that comprise host cell proteins (HCP), DNA, high molecular weight species (HMW), low molecular weight species (LMW), residual Protein A (rPA) or any combination thereof. In some embodiments, the chromatography reduces (i) DNA to a level of about 20 pg/mL or lower, (ii) LMWs to a level of about 1.0% or lower, (iii) EMWs to a level of about 1.0% or lower, (iv) HCP to a level of about 100 ppm or lower, (v) residual Protein A (rPA) to a level of about 6 ppm or lower, or any combination thereof.

In some embodiments, the chromatography reduces the DNA to a level of about 20 pg/mL or lower, about 18 pg/mL or lower, about 16 pg/mL or lower, about 14 pg/mL or lower, about 12 pg/mL or lower, about 10 pg/mL or lower, about 8 pg/mL or lower, about 6 pg/mL or lower, about 4 pg/mL or lower, or about 2 pg/mL or lower.

In some embodiments, the chromatography reduces the low molecular weight species (LMW) to a level of about 1.0% or lower, about 0.9% or lower, about 0.8% or lower, about 0.7% or lower, about 0.6% or lower, about 0.5% or lower, about 0.4% or lower, about 0.3% or lower, about 0.2% or lower or about 0.1% or lower.

In some embodiments the chromatography reduces the high molecular weight species (UMW) to a level of about 1.0% or lower, about 0.9% or lower, about 0.8% or lower, about 0.7% or lower, about 0.6% or lower, about 0.5% or lower, about 0.4% or lower, about 0.3% or lower, about 0.2% or lower or about 0.1% or lower.

In some embodiments the chromatography reduces the host cell protein (HCP) to a level of about 100 ppm or lower, about 90 ppm or lower, about 80 ppm or lower, about 70 ppm or lower, about 60 ppm or lower, about 50 ppm or lower, about 40 ppm or lower, about 30 ppm or lower, about 20 ppm or lower, or about 10 ppm or lower.

In some embodiments the chromatography reduces the residual Protein A (rPA) to a level of about 6 ppm or lower, about 5 ppm or lower, about 4 ppm or lower, about 3 ppm or lower, about 2 ppm or lower , about 1 ppm or lower, about 0.8 ppm or lower, about 0.6 ppm or lower, about 0.5 ppm or lower, about 0.4 ppm or lower, about 0.3 ppm or lower, about 0.2 ppm or lower or about 0.1 ppm or lower.

In some embodiments, the method of the present disclosure is performed after one or more downstream purifications, e.g., filtration, affinity chromatography, tangential flow chromatography, viral inactivation, or any combination thereof. In other embodiments, the method of the present disclosure is performed without any purification step after harvest. In other embodiments, the chromatography of the present disclosure is the last step prior to viral inactivation. In yet other embodiments, the method of the present disclosure can concomitantly inactivate one or more viruses. In still other embodiments, the method of the present disclosure further comprises a viral inactivation step before or after the combined AEX and CEX or CEX and AEX chromatography.

III. Methods of Removing Buffer Transition Peak

The present disclosure also includes a method of removing or reducing a buffer transition peak between the loading buffer and the chase buffer. To remove or reduce the buffer transition peak in a chromatography, e.g., an AEX, a CEX, a combined AEX and CEX, a combined CEX and AEX, optionally in flow-through mode, the method comprises adding a loading buffer and adding a chase buffer, wherein the chase buffer has a higher conductivity compared to the loading buffer. In some embodiments, the chromatography is a combined AEX and CEX or a combined CEX and AEX chromatography.

In some embodiments, the conductivity of the chase buffer is at least 0.5 mS/cm, at least 0.6 mS/cm, at least 0.7 mS/cm, at least 0.8 mS/cm, at least 0.9 mS/cm, at least 1.0 mS/cm, at least 1.1 mS/cm, at least 1.2 mS/cm, at least 1.3 mS/cm, at least 1.4 mS/cm, at least 1.5 mS/cm, at least 1.6 mS/cm, at least 1.7 mS/cm, at least 1.8 mS/cm, at least 1.9 mS/cm, at least 2.0 mS/cm, at least 2.1 mS/cm, at least 2.2 mS/cm, at least 2.3 mS/cm, at least 2.4 mS/cm, at least 2.5 mS/cm, at least 2.6 mS/cm, at least 2.7 mS/cm, at least 2.8 mS/cm, at least 2.9 mS/cm, at least 3.0 mS/cm, at least 3.1 mS/cm, at least 3.2 mS/cm, at least 3.3 mS/cm, at least 3.4 mS/cm, at least 3.5 mS/cm, at least 3.6 mS/cm, at least 3.7 mS/cm, at least 3.8 mS/cm, at least 3.9 mS/cm, at least 4.0 mS/cm, at least 4.1 mS/cm, at least 4.2 mS/cm, at least 4.3 mS/cm, at least 4.4 mS/cm, at least 4.5 mS/cm, at least 4.6 mS/cm, at least 4.7 mS/cm, at least 4.8 mS/cm, at least 4.9 mS/cm, or at least 5.0 mS/cm, higher than the conductivity of the loading buffer. In other embodiments, the conductivity of the loading buffer is about 1.0 mS/cm higher than that of the chase buffer.

In some embodiments, the loading buffer has a conductivity lower than the chase buffer. In some embodiments, the conductivity of the loading buffer is at least 0.5 mS/cm, at least 1.0 mS/cm, at least 1.5 mS/cm, at least 2.0 mS/cm, at least 2.5 mS/cm, at least 3.0 mS/cm, at least 3.5 mS/cm, at least 4.0 mS/cm, at least 4.5 mS/cm, or at least 5.0 mS/cm, lower than the conductivity of the chase buffer. In other embodiments, the conductivity of the loading buffer is about 1.0 mS/cm lower than that of the chase buffer.

In some embodiments, the methods of removing or reducing a buffer transition peak in (III) can be combined with the methods of purifying a protein of (II). Therefore, in some embodiments, the present disclosure includes a method of purifying a protein of interest in a mixture comprising performing a combined AEX and CEX or a combined CEX and AEX chromatography under an operating condition (e.g., pH and/or conductivity) wherein no automation, engineering control, and/or in-line adjustment is used between the AEX and the CEX and wherein the chase buffer used in the chromatography has a higher conductivity than the loading buffer used in the chromatography.

Protein of Interest

The methods (II) and/or (III) of the present disclosure can be used to isolate or purify any protein of interest, e.g., naturally occurring or non-naturally occurring proteins, recombinantly produced or plasma purified proteins, or any combination thereof. The protein of interest can be in a mixture with one or more contaminants as described elsewhere herein. In some embodiments, the protein of interest has already been gone through downstream purifications, e.g., filtration, affinity chromatography, tangential flow chromatography, viral inactivation, a polishing step, or any combination thereof. In other embodiments, the protein of interest is in a mixture with contaminants and has not gone through any purification step after harvest.

In some embodiments, the mixture contains a protein of interest that is an antibody.

In some embodiments, the protein of interest is a fusion protein comprising a protein of interest and a heterologous moiety. In other embodiments, a fusion protein to be isolated or purified by the present methods is an Fc fusion protein. In other embodiments, a protein to be isolated or purified by the present methods is a pegylated, hesylated, or sialylated protein.

In other embodiments, the protein of interest is produced in a host cell. In some embodiments, the protein of interest is produced in culture comprising mammalian cells. In some embodiments, the mammalian cells are Chinese hamster ovary (CHO) cells, HEK293 cells, mouse myeloma (NSO), baby hamster kidney cells (BHK), monkey kidney fibroblast cells (COS-7), Madin-Darby bovine kidney cells (MDBK) or any combination thereof. In some embodiments, the starting mixture can be a harvested cell culture fluid, a cell culture supernatant, a conditioned cell culture supernatant, a cell lysate, and a clarified bulk.

In some embodiments, the cell culture has been subject to one or more downstream purification methods, e.g., an affinity chromatography selected from a protein A affinity chromatography and a protein G affinity chromatography. In other embodiments, the starting mixture for the present methods has been run through one or more downstream purification, e.g., diafiltration, ultrafiltration, affinity chromatography, tangential flow chromatography, viral inactivation, or any combination thereof.

The present disclosure is further illustrated by the following examples which should not be construed as further limiting. The contents of all references cited throughout this application are expressly incorporated herein by reference.

EXAMPLES

Example 1

Evaluation of Polishing

To evaluate the polishing step sequences and possible combined polishing step as well as effectiveness of the reduction on unwanted contaminants, different polishing scenarios were studied as shown in Table 1. The loading materials for the study is protein A elution and neutralization pool (PAVIN) at pH 5.5 (without depth filtration). Before each run, the PAVIN pool is pH adjusted to 7.2 using 2M Tris. As shown in Table 1, CEX (F/T) can effectively remove HMW and rPA; AEX (F/T) greatly reduce the HCP, but is unable to remove rPA and HMW. Using two step polishing (CEX (F/T) followed by AEX (F/T)), HCP, HMW, rPA levels are all reduced to a relatively low level. Combined CEX-AEX F/T was also evaluated here by connecting the two column together and operated using the CEX F/T conditions (load at pH 7.2 and 5 mS/cm, chase at pH 7.2 and 6 mS/cm). The outlet of a POROS XS column (10 cm bed height, 0.66 cm inner diameter) was directly connected to the inlet of a Capto Q column (10 cm bed height, 0.66 cm inner diameter) without any automation or engineering control between the two columns as shown in FIG. 1.

To evaluate the effectiveness of the combined CEX/AEX F/T (AEX/CEX F/T) polishing steps without any adjustments, the starting mixture, "Protein A Elution and Neutralization Pool" (PAVIN), had a pH of 5.5 and contained the impurities listed in Table 1. Reduction in unwanted contaminants after a variety of chromatographic approaches is detailed in Table 1. CEX alone, AEX alone, combined CEX-AEX with conductivity adjustment and combined CEX-AEX followed by AEX-CEX without any adjustment were tested with the operating conditions listed above. All chromatography was operated in flow-through mode.

The combined CEX-AEX or AEX-CEX F/T polishing step without any adjustments shows great removal of HCP, rPA and BMW with reduced operation time/cost and skid footprint. A number of advantages of the combined CEX-AEX or AEX-CEX F/T polishing were shown; they include significantly reduced operation time, cost and skid footprint compared to single F/T polishing unit as well as combined CEX (F/T) and AEX (F/T) polishing steps with conductivity adjustment between the CEX and the AEX. The combined CEX-AEX or AEX-CEX without any pH and conductivity adjustment greatly improved the downstream productivity compared to single F/T polishing units. Both CEX and AEX (F/T) can work with high loading (≥300 g/L). The combined CEX and AEX or AEX and CEX chromatography without any pH and conductivity adjustment can utilize the same buffer system: Same Charge, EQ, Strip, Sanitization and storage buffer for CEX and AEX. The current chromatography can also be implemented simply by connecting the outlet of CEX to the AEX inlet directly as shown in FIG. 1.

TABLE 1

| | | HCP (ppm) | HMW (%) | LMW (%) | DNA (pg/mL) | rPA (ppm) |
|---|---|---|---|---|---|---|
| | Different scenario polishing steps evaluation. | | | | | |
| Step | Operating conditions | | | | | |
| PAVIN | Load | 209 | 1.4 | 0.2 | <10 | 6 |
| CEX (F/T) POROS XS | pH 7.2, conductivity 5 mS/cm | 75 | 0.4 | 0.3 | <10 | 2 |
| AEX (F/T) Capto Q | pH 7.2, conductivity 1.7 mS/cm | 20 | 1.5 | 0.2 | <10 | 6 |
| CEX (F/T)-AEX (F/T) | CEX (pH 7.2, conductivity 5 mS/cm, chase with pH 7.2, 6 mS/cm), AEX (dilute to pH 7.2, conductivity 3 mS/cm) | 9 | 0.4 | 0.2 | <10 | 2 |
| Combined CEX-AEX (F/T) and combined AEX-CEX (F/T) | pH 7.2, conductivity 5 mS/cm, chase with pH 7.2, 6 mS/cm buffer | 24 | 0.3 | 0.2 | <10 | 2 |

Example 2

Summary of Molecules Evaluated with CEX-AEX F/T Polishing

The purification efficacy was measured for a number of antibodies with various isoelectric points (pI), and is detailed in Table 2. The first four antibodies were purified using a pH below their isoelectric point, indicating that the antibody was carrying a slightly positive net charge during chromatography. In order to prevent binding of the antibodies to the column and promote their flow-through, salt was used to increase the conductivity of the buffers to a level where the antibody of interest was not strongly retained on the columns, but the undesirable contaminants such as HCP, rPA, and HMW were retained. In the case of the fifth antibody, with a pI of 5.8, higher salt concentrations were used to prevent interactions of the negative-charge carrying antibody and the anion exchange resin.

TABLE 2

| Molecule | pI | Isotype | Combined CEX-AEX F/T polishing | Materials | Operating conditions | Load HCP (ppm) | Load rPA (ppm) | Load HMW (%) | Elution pool HCP (ppm) | Elution pool rpA (ppm) | Elution pool HMW (%) |
|---|---|---|---|---|---|---|---|---|---|---|---|
| | | | | | Summary Of Molecules Evaluated With CEX-AEX F/T Polishing Step | | | | | | |
| Antibody-1 | 8.4 | IgG1 | CEX-AEX (POROS XS-Capto Q) | Antibody-1 Protein A Elution and Neutralization Pool (PAVIB) | Load at pH 7.2, 2.7 mS/cm, chase at pH 7.2, 3 mS/cm | 35 | 4 | 0.8 | 5 | 0.6 | 0.5 |
| Antibody-2 | 9.2 | IgG1 | CEX-AEX (POROS XS-Capto Q) | Antibody-2 Protein A Elution and Neutralization Pool (PAVIB) | Load at pH 7.2, 6.8 mS/cm, chase at pH 7.2, 6.8 mS/cm | 65 | 2.8 | 1.4 | 8 | 0.3 | 0.6 |
| Antibody-3 | 7.6 | IgG4 | CEX-AEX (POROS XS-Capto Q) | Antibody-3 Protein A Elution and Neutralization Pool (PAVIB) | Load at pH 7.4, 3.2 mS/cm, chase at pH 7.4, 5.5 mS/cm | 36 | 3.3 | 1.9 | 12 | 0.3 | 0.4 |
| Antibody-4 | 8.9 | IgG1 | CEX-AEX (POROS XS-POROS HQ) | Antibody-4 Protein A Elution and Neutralization Pool (PAVIB) | Load at pH 8.0, 3.0 mS/cm, chase at pH 8.0, 4.5 mS/cm | 188 | 7.8 | 1.8 | 8 | 0.2 | 1.0 |
| Antibody-5 | 5.8 | IgG4 | CEX-AEX (POROS XS-Capto Q) | Antibody-5 Protein A Elution and Neutralization Pool (PAVIB) | Load at pH 7.0, 9.2 mS/cm, chase at pH 7.0, 12.0 mS/cm | 263 | 0.1 | 4.2 | 84 | <0.1 | 2.1 |

Figure 2:
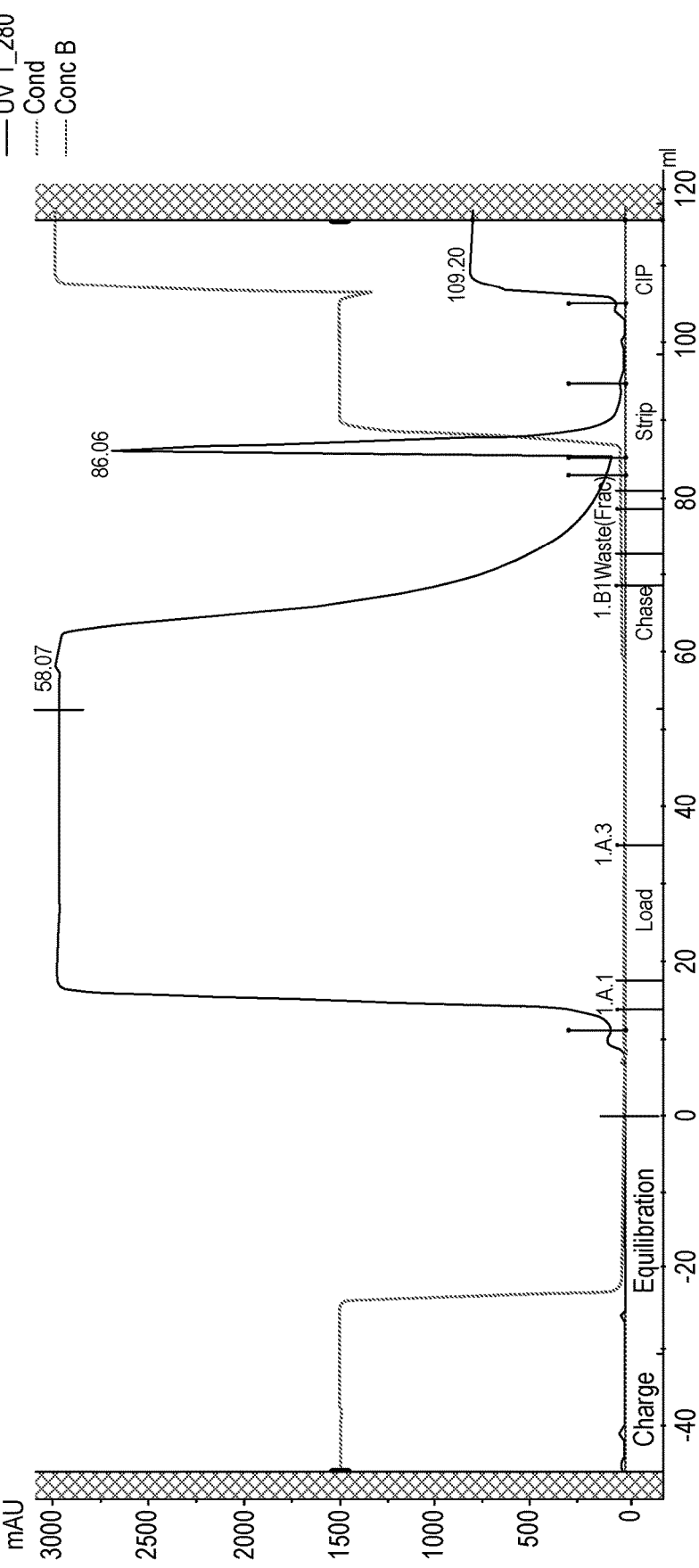
FIG. 2 shows a representative chromatogram of combined CEX-AEX F/T polishing at a conductivity of 5 mS/cm at a pH of 7.2.

A representative chromatogram for combined CEX-AEX F/T polishing step without any adjustments is shown in FIG. 2.

Example 3

Evaluation of Buffer Transition Induced Post-Loading Peak

Figure 3A:
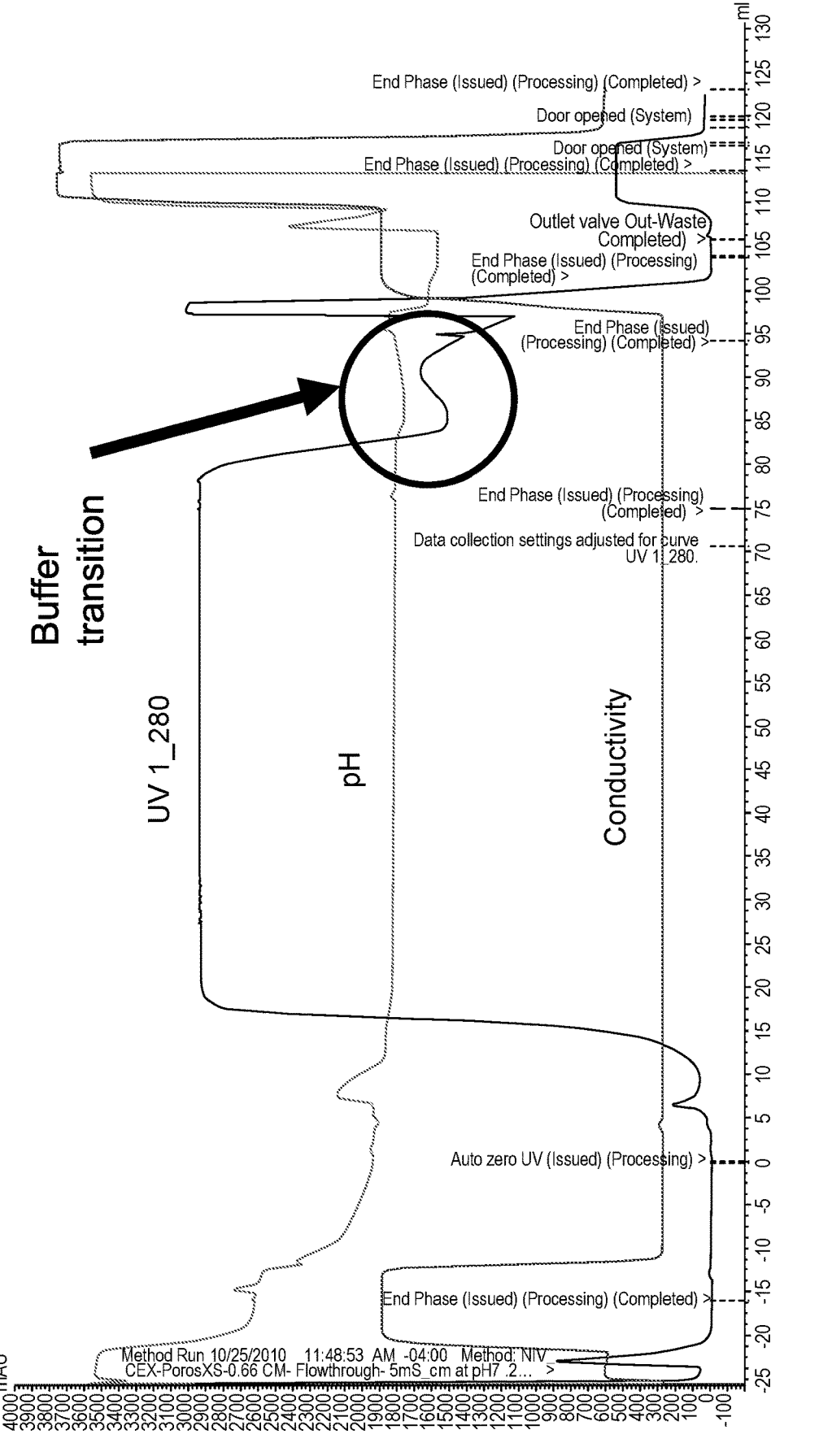
FIG. 3A shows a chromatogram of CEX F/T loading and chase at 5 mS/cm, pH 7.2. The loading buffer and chase buffer has similar pH and conductivity using sodium Acetate-Tris buffer system. A buffer transition induced post-loading peak, as measured by absorbance at 280 nm, was observed after adding chase buffer.
Figure 3B:
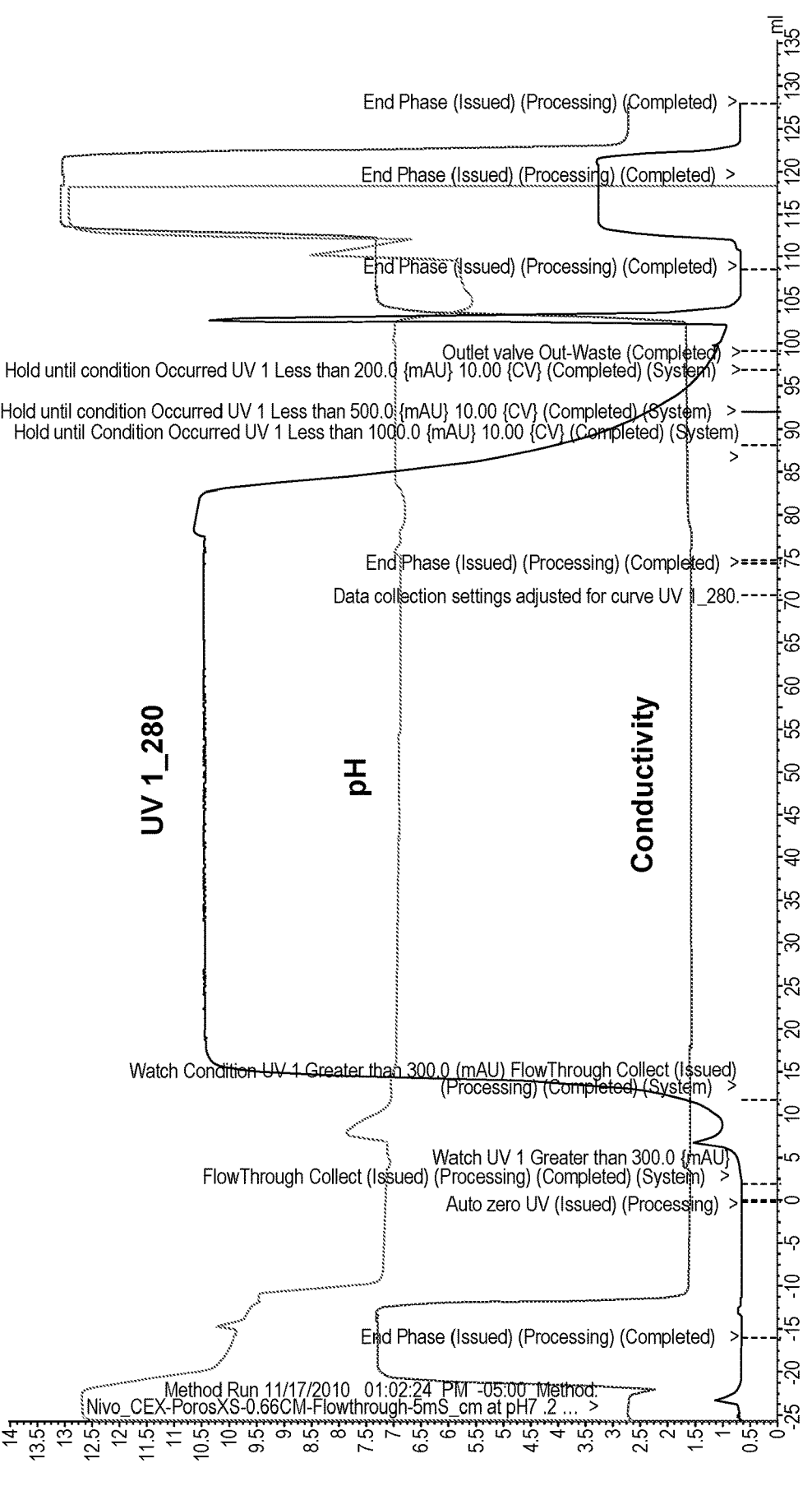
FIG. 3B shows a chromatogram of CEX F/T loading at 5 mS/cm pH 7.2 and chase at 6 mS/cm pH 7.2. Higher conductivity buffer used during chase can effectively remove the post-loading peak.

A protein mixture containing Antibody-3 was run through a CEX (F/T) to evaluate its effectiveness in isolating this antibody. The CEX F/T was run at pH of 7.2 with 5 mS/cm loading buffer and 5 mS/cm chasing buffer. Both buffers contain Sodium Acetate-Tris buffer. Protein elution was measured via light absorbance at 280 nm. A transition from loading buffer to chase buffer induced an unwanted, post buffer transition peak as shown in FIG. 3A. when the CEX F/T was performed again with the only change in the chase buffer conductivity, i.e., 6 mS/cm, which is 1 mS/cm increase, the chromatogram showed that the post buffer transition peak disappeared as shown in FIG. 3B. Therefore, by increasing the conductivity of the chase buffer, the peak due to the transition from loading buffer to chase buffer can be reduced or removed.

Throughout this application, various publications are referenced in parentheses by author name and date, or by Patent No. or Patent Publication No. The disclosures of these publications are hereby incorporated in their entireties by reference into this application in order to more fully describe the state of the art as known to those skilled therein as of the date of the disclosure described and claimed herein. However, the citation of a reference herein should not be construed as an acknowledgment that such reference is prior art to the present disclosure.

What is claimed is:

1. A method of purifying an antibody from a mixture comprising one or more contaminants, the method comprising performing a combined chromatography, the combined chromatography comprises a combined cation exchange chromatography (CEX) and anion exchange chromatography (AEX) in flow-through mode or a combined AEX and CEX in flow-through mode wherein no automation, engineering control, and in-line adjustment are used between the CEX and the AEX or the AEX and the CEX, wherein operating conditions (pH and conductivity) between the CEX and the AEX or the AEX and CEX are not adjusted, wherein the CEX and the AEX or the AEX and the CEX are connected directly, wherein the mixture was isolated by protein A affinity chromatography prior to performing the combined chromatography, wherein the combined chromatography comprises adding a loading buffer and adding a chase buffer, wherein the pH of the chase buffer is the same as the pH of the loading buffer and the conductivity of the chase buffer is higher than the conductivity of the loading buffer, wherein the pH is selected based on the isoelectric point (pI) of the antibody and wherein the combined chromatography reduces the level of contaminants in the mixture, wherein the contaminants comprise host cell proteins (HCP), DNA, high molecular weight species (HMW), low molecular weight species (LMW), and residual protein A (rPA), and wherein the operating conditions (pH and conductivity) of the combined chromatography are selected such that it reduces the HCP level to about 20 ppm or lower and the rPA level to 0.6 ppm or lower.

2. The method of claim 1, wherein the antibody has an isoelectric point (pI) between about 6.5 and about 12.0.

3. The method of claim 1, wherein the antibody has an isoelectric point (pI) between 1.0 and about 6.5.

4. The method of claim 1, wherein the pH of the loading buffer is between about 6.0 and about 14.0.

5. The method of claim 1, wherein the pH of the chase buffer is between about 6.0 and about 14.0.

6. The method of claim 1, wherein the conductivity of the loading buffer is between about 0.1 mS/cm and about 9.0 mS/cm.

7. The method of claim 1, wherein the conductivity of the chase buffer is between about 0.1 mS/cm and about 9.0 mS/cm.

8. The method of claim 1, wherein the conductivity of the chase buffer is between about 0.2 mS/cm and about 15.0 mS/cm and wherein the conductivity of the chase buffer is at least 0.1 mS/cm higher than the conductivity of the loading buffer.

9. The method of claim 1, wherein the combined chromatography reduces:

(a) the HCP level to about 10 ppm or lower;

(b) the HMW level to about 1.0% or lower;

(c) the LMW level to about 1.0% or lower;

(d) the DNA level to about 20 pg/mL or lower; and/or (e) the rPA level to about 0.5 ppm or lower.

10. The method of claim 1, wherein the antibody comprises full-length antibody or an antibody fragment.

11. The method of claim 1, wherein the antibody is an isotype comprising IgM, IgA, IgE, IgD, or IgG.

12. The method of claim 1, wherein the CEX comprises a cation exchange resin comprising a sulfonate based group, a sulfoethyl based group, a sulphopropyl based group, a sulfoisobutyl based group, a sulfoxyethyl based group, a carboxymethyl based group, sulfonic and carboxylic acid based groups, a carboxylic acid based group, a sulfonic acid based group, or a orthophosphate based group.

\* \* \* \* \*